United States Patent
Dadachova (10) Patent No.: US 7,709,613 B2
(45) Date of Patent: May 4, 2010

(54) RHENIUM-188 AND RHENIUM-186 FOR TREATMENT OF TUMORS EXPRESSING A NA⁺/I⁻ SYMPORTER

(75) Inventor: Ekaterina Dadachova, Mahopac, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 184 days.

(21) Appl. No.: 10/704,434

(22) Filed: Nov. 7, 2003

(65) Prior Publication Data

US 2004/0120890 A1    Jun. 24, 2004

Related U.S. Application Data

(60) Provisional application No. 60/427,150, filed on Nov. 18, 2002.

(51) Int. Cl.
*A61K 51/04* (2006.01)
(52) U.S. Cl. .................. 534/10; 424/1.11; 424/1.65; 424/1.81; 424/9.1
(58) Field of Classification Search ............... 424/1.11, 424/1.65, 9.1, 9.2, 1.18; 514/1; 534/10, 534/14
See application file for complete search history.

(56) References Cited

U.S. PATENT DOCUMENTS

| | | | | |
|---|---|---|---|---|
| 5,620,675 | A * | 4/1997 | McBride et al. | 424/1.69 |
| 6,331,285 | B1 * | 12/2001 | Sharma | 424/1.69 |
| 6,821,725 | B1 * | 11/2004 | Carrasco et al. | 435/6 |
| 7,060,247 | B2 * | 6/2006 | Hoffman et al. | 424/9.1 |

FOREIGN PATENT DOCUMENTS

WO    WO 01/65998 A2    9/2001

OTHER PUBLICATIONS

Dadachova et al, Nuclear Medicine and Biology, Jan. 2002, vol. 29, pp. 13-18.*
Elements of General, Organic, and Biological Chemistry, Ninth Edition, 1995, pp. 42-47, by John Holum.*
Golub et al., Science, Oct. 15, 1999, pp. 531-537.*
Shen, DH et al. "188Re-Perrhenate Treatment to Enhance the Survival of Rats Bearing Intracerebral Sodium-Iodide Symporter Transduced Gliomas," Proceedings of the SNM 50th Annual Meeting, J. Nuclear Medicine, vol. 44, No. 5, p. 35P, May 2003 Supplement.
Eskandar, Sepehr et al., entitled "Thyroid Na+/I–Symporter," The Journal of Biological Chemistry, vol. 272, No. 43, Issue of Oct. 24, pp. 27230-27238, 1997.
Kilbane, M. T. et al., entitled "Tissue Iodine Content and Serum-Mediated 125I Uptake-Blocking Activity in Breast Cancer," The Journal of Endocrinology & Metabolism, vol. 85, No. 3, pp. 1245-1250, 2000.
Spitzweg, C. et al., entitled "Analysis of Human Sodium Iodide Symporter Gene Expression in Extrathyroidal Tissues and Cloning of Its Complementary Deoxyribonucleic Acids from Salivary Gland, Mammary Gland, and Gastric Mucosa," The Journal of Endocrinology & Metabolism, vol. 83, No. 5, pp. 1746-1751, 1998.
Sptizweg, C. et al., entitled "Treatment of Prostate Cancer by Radioiodine Therapy after Tissue-specific Expression of the Sodium Iodide Symporter," Cancer Research 60, 6526-6530. Nov. 15. 2000.
Cancroft, Elizabeth T. et al., entitled "99m Tc-Pertechnetate Scintigraphy as an Aid in the Diagnosis of Breast Masses," Radiology, vol. 106, No. 2, pp. 441-444, Feb. 1973.
Tazebay, Uygar H. et al., entitled "The mammary gland iodide transporter is expressed during lactation and in breast cancer," Nature Medicine, vol. 6, No. 8, pp. 871-878, Aug. 2000.
Dadachova E et al., entitled "Treatment with rhenium-188-perrhenate and iodine-131 of NIS-expressing mammary cancer in a mouse model remarkably inhibited tumor growth," Nuclear Medicine and Biology, 32 (2005), pp. 695-700.

* cited by examiner

*Primary Examiner*—D L Jones
(74) *Attorney, Agent, or Firm*—Amster, Rothstein and Ebenstein LLP (57) ABSTRACT

This invention provides methods of using Rhenium radioisotopes to detect and treat tumors that express a Na⁺/I⁻ symporter. The invention also provides compositions and methods of making compositions comprising Rhenium radioisotopes for detection and treatment of tumors that express a Na⁺/I⁻ symporter.

10 Claims, 5 Drawing Sheets

RHENIUM-188 AND RHENIUM-186 FOR TREATMENT OF TUMORS EXPRESSING A NA$^+$/I$^-$ SYMPORTER

PRIORITY CLAIM

This application claims the benefit of U.S. Provisional Application No. 60/427,150, filed Nov. 18, 2002, the content of which is hereby incorporated by reference in its entirety into the subject application.

STATEMENT OF GOVERNMENT SUPPORT

The invention disclosed herein was made with U.S. Government support under grant numbers R01CA70897, R01CA75503, R01CA77552, and 5-P30-CA13330-26 from the National Institutes of Health, U.S. Department of Health and Human Services. Accordingly, the U.S. Government has certain rights in this invention.

FIELD OF THE INVENTION

The present invention relates to the use of Rhenium radioisotopes to detect and treat tumors that expresses a Na$^+$/I$^-$ symporter.

BACKGROUND OF THE INVENTION

Throughout this application various publications are referred to in parenthesis or brackets. Full citations for these references may be found at the end of the specification immediately preceding the claims. The disclosures of these publications are hereby incorporated by reference in their entireties into the subject application to more fully describe the art to which the subject application pertains.

Breast cancer remains the major cause of cancer death in women in the developed world. Novel therapeutic modalities are needed for patients with tumors resistant to conventional therapies such as chemotherapy, hormonal treatment and external radiation. Recently Tazebay et al. [31, 41] found that more than 80% of human mammary cancers, but not normal healthy non-lactating breast tissue, express a sodium/iodide symporter (NIS) which was named the mammary gland NIS (mgNIS). Kilbane et al. [11] found NIS expression to be a feature of both fibroadenomata and breast carcinoma tissues.

NIS mediates iodide accumulation in the thyroid gland [2], and the capability to concentrate and organify iodide allows the use of radioactive iodine isotope $^{131}$I for the treatment of differentiated thyroid cancers and hyperthyroidism [10, 24]. However, as pointed out by Daniels and Harber [5], organification of iodide is unlikely to occur in breast cancer cells as the thyroid is the only organ known to organify iodide, a process that involves the conversion of inorganic iodide to an organic form by conjugation to tyrosine residues on the protein thyroglobulin, a precursor to iodinated forms of thyroid hormone [30]. The organification process causes radioiodine to be retained within the thyroid gland for several days [16]. This relatively long retention time matches the physical half-life of $^{131}$I (8 days) and allows a significant radiation dose to be delivered to the tumor.

NIS gene expression has been detected in several tissues in humans, including the thyroid gland, mammary gland, salivary glands, and gastric mucosa [43].

Several studies have reported transfection of NIS into different non-thyroid or undifferentiated thyroid tumors for the purpose of subsequent therapy with $^{131}$I [1, 3, 15, 17, 21, 27]. In all of these studies, although $^{131}$I uptake in NIS-expressing tumors was substantial (up to 27% injected dose in [27]), the residence times of $^{131}$I in the tumors were relatively short and no tumor shrinkage was observed [1, 3, 27]. In a recent report by Spitzweg et al. [28], impressive therapeutic results were seen in NIS-transfected prostate tumor xenografts in mice when treated with a very high single 3 mCi dose of $^{131}$I. However, as no biodistribution and no dose-escalation studies were reported, it is unclear why such high dose was administered. The lack of therapeutic gains observed by other investigators [1, 3, 27] can be attributable to the long physical half-life (8 days) and decay properties of $^{131}$I, as the beta-particles emitted by $^{131}$I are low energy ($E_{average}$=0.134 MeV) and have an optimal tissue range of only 2.6-5.0 mm [22].

Several different approaches to circumvent the problem of insufficient iodide radiation dose to NIS-expressing tumors have been suggested. Daniels and Haber [5] and Nakamoto [21] suggested that pharmacologic modulation of fast cellular radioiodide efflux from breast cancer cells might be possible by administering lithium salts which increase radioiodide half-life in thyroid tumors. Boland et al. [1] proposed to improve the efficiency of NIS gene transfer and thus the iodide uptake capacity of the target tissue by the use of modified vectors and/or higher viral doses. The same authors also proposed to increase the biological half-life of radioiodide in the tumor tissues by coupling transfer of the NIS gene with the delivery of a gene involved in the iodide organification process, such as thyroperoxidase. Such an approach is not easy to implement because of the inherent complexity of gene therapy procedures especially in the case of 2-gene transfer and the difficulty in transfecting only the target tissue (tumor) in vivo.

A short-lived isotope of technetium $^{99m}$Tc is used in ~90% of all diagnostic nuclear medicine procedures [e.g., 42]. It has long been recognized by nuclear medicine practitioners that due to their common ionic characteristics, iodide and $^{99m}$Tc-pertechnetate ($^{99m}$TcO$_4^-$) behave similarly following intravenous administration [23]. Like iodide, $^{99m}$TcO$_4^-$ localizes in the thyroid, salivary glands, gastric mucosa, and choroid plexus of the brain. It is trapped but not organified in the thyroid gland and is used in nuclear medicine as an alternative to Na$^{123}$I for assessing thyroid condition.

Rhenium is a chemical analogue of technetium and exhibits practically identical chemical and biodistribution properties [6]. 188-Rhenium ($^{188}$Re), a powerful beta-emitting radionuclide ($E_{average}$=0.764 MeV) with a 16.7 hour half-life has been recently used in a number of therapeutic applications in humans including cancer radioimmunotherapy, palliation of skeletal bone pain, and endovascular brachytherapy to prevent restenosis after angioplasty [8, 12, 25], as well as in the pre-clinical development of novel therapeutics [4, 19]. 186-Rhenium ($^{186}$Re), which has a half-life of 3.7 days and $E_{average}$=0.362 MeV, is also being used in clinical applications [33-36]. Because of its chemical similarity to pertechnetate, the perrhenate anion ($^{188}$ReO$_4^-$) is concentrated in thyroid and stomach [14]. Co-injected $^{99m}$TcO$_4^-$, $^{125}$I$^-$, and $^{188}$ReO$_4^-$ have similar uptake and biodistribution in NIS-expressing (thyroid, stomach, salivary gland) and non-expressing tissues in normal, healthy mice, with the exception of the thyroid gland where only $^{125}$I$^-$ is retained by organification [32]. In contrast, a study employing rat thyroid NIS expressed in Xenopus laevis oocytes found that ReO$_4^-$ is a potent blocking agent for NIS, second to only perchlorate (ClO$_4^-$), and that ReO$_4^-$ is transported via NIS only to a very small extent and only when the concentration of ReO$_4^-$ is high [44]. Accordingly, the ability of NIS to mediate the transport of $ReO_4^-$ in general, and its potential for doing so in tumor cells in particular, have not been resolved.

SUMMARY OF THE INVENTION

The present application demonstrates that tumors expressing a $Na^+/I^-$ symporter uptake powerful beta-emitting Rhenium radioisotopes, a finding that is significant for the diagnosis and treatment of cancer.

The subject invention is directed to a method of treating a tumor that expresses a $Na^+/I^-$ symporter in a subject which comprises administering to the subject an amount of a Rhenium radioisotope effective to treat the tumor, wherein the Rhenium radioisotope is 188-Rhenium or 186-Rhenium, in particular $^{188}ReO_4^-$ or $^{186}ReO_4^-$.

The invention also provides a method for diagnosing the presence of a tumor that expresses a $Na^+/I^-$ symporter in a subject which comprises administering a Rhenium radioisotope to the subject's tumor and detecting the uptake of the Rhenium radioisotope by the tumor, wherein the Rhenium radioisotope is 188-Rhenium or 186-Rhenium, in particular $^{188}ReO_4^-$ or $^{186}ReO_4^-$.

The invention provides a method of making a composition for treating a tumor that expresses a $Na^+/I^-$ symporter in a subject, which comprises admixing a Rhenium radioisotope and a carrier, wherein the Rhenium radioisotope is 188-Rhenium or 186-Rhenium, in particular $^{188}ReO_4^-$ or $^{186}ReO_4^-$. The invention also provides a composition for treating a tumor that expresses a $Na^+/I^-$ symporter in a subject, which comprises a Rhenium radioisotope and a carrier, wherein the Rhenium radioisotope is 188-Rhenium or 186-Rhenium, in particular $^{188}ReO_4^-$ or $^{186}ReO_4^-$.

DETAILED DESCRIPTION OF THE INVENTION

The subject invention is directed to a method of treating a tumor that expresses a $Na^+/I^-$ symporter in a subject which comprises administering to the subject an amount of a Rhenium radioisotope effective to treat the tumor, wherein the Rhenium radioisotope is 188-Rhenium or 186-Rhenium. In different embodiments, the subject is treated using $^{188}ReO_4^-$ or $^{186}ReO_4^-$.

As used herein, the term "treat" a tumor means to eradicate the tumor, to reduce the size of the tumor, to stabilize the tumor so that it does not increase in size, or to reduce the further growth of the tumor.

In a preferred embodiment, the tumor is a breast tumor. In different embodiments, the tumor is a thyroid tumor or a gastrointestinal tract tumor. In one embodiment, the subject is not a lactating subject.

The Rhenium radioisotopes deliver a superior radiation dose to the tumor in comparison to radioactive iodine. The radiation dose that is delivered to the tumor using the Rhenium radioisotope is higher than the radiation dose that could be delivered to the tumor using an iodine radioisotope, where the concentration of the Rhenium radioisotope administered to the subject is the same as the concentration of the iodine radioisotope administered to the subject. Preferably, the radiation dose that is delivered to the tumor using the Rhenium radioisotope is at least four-fold higher than the radiation dose that could be delivered to the tumor using an iodine radioisotope, where the concentration of the Rhenium radioisotope administered to the subject is the same as the concentration of the iodine radioisotope administered to the subject. In one embodiment, the radiation dose that is delivered to the tumor using the Rhenium radioisotope is 4.5 times higher than the radiation dose that could be delivered to the tumor using an iodine radioisotope, where the concentration of the Rhenium radioisotope administered to the subject is the same as the concentration of the iodine radioisotope administered to the subject.

The $Na^+/I^-$ symporter can be transfected into tumor cells. In one embodiment, the tumor into which NIS is transfected is a prostate tumor. Methods for transfection of $Na^+/I^-$ symporter into tumors are well known in the art [1, 3, 15, 17, 21, 27, 28]. In one embodiment, the $Na^+/I^-$ symporter is transfected into tumor cells by direct injection into the tumor. Nucleic acid encoding the $Na^+/I^-$ symporter can be used, or $Na^+/I^-$ symporter protein can be used.

The Rhenium radioisotope can be administered in a single dose or in a fractionated manner. In different embodiments, the cumulative dose is between 0.5-500 mCi.

The invention also provides a method for diagnosing the presence of a tumor that expresses a $Na^+/I^-$ symporter in a subject which comprises administering a Rhenium radioisotope to the subject's tumor and detecting the uptake of the Rhenium radioisotope by the tumor, wherein the Rhenium radioisotope is 188-Rhenium or 186-Rhenium. In different embodiments, the Rhenium radioisotope is administered as $^{188}ReO_4$, or $^{186}ReO_4^-$. Procedures for nuclear medicine imaging are well known in the art [23, 37]. The Rhenium radioisotope can be administered in vivo. The Rhenium radioisotope can also be administered to a tissue biopsy obtained from the subject. The tissue biopsy can be analyzed for the presence of a $Na^+/I^-$ symporter using immunohistochemistry [31, 41]. In a preferred embodiment, the tumor is a breast tumor and the subject is a non-lactating subject.

Gastric lavage can be used to decrease the binding of the Rhenium radioisotope to a $Na^+/I^-$ symporter in the gastric mucosa. Methods for gastric lavage are well known in the art [38]. Exogenous thyroid hormone can be administered to the subject to decrease the binding of the Rhenium radioisotope to a $Na^+/I^-$ symporter in the thyroid, using procedures that are well known in the art [39].

The invention provides a method of making a composition for treating a tumor that expresses a $Na^+/I^-$ symporter in a subject, which comprises admixing a Rhenium radioisotope and a carrier, wherein the Rhenium radioisotope is 188-Rhenium or 186-Rhenium. In different embodiments, the Rhenium radioisotope is $^{188}ReO_4^-$ or $^{186}ReO_4^-$. The invention also provides a composition made according to this method.

The invention also provides a composition for treating a tumor that expresses a $Na^+/I^-$ symporter in a subject, which comprises a Rhenium radioisotope and a carrier, wherein the Rhenium radioisotope is 188-Rhenium or 186-Rhenium. In different embodiments, the Rhenium radioisotope is $^{188}ReO_4^-$ or $^{186}ReO_4^-$.

As used herein, the term "carrier" encompasses any of the standard pharmaceutical carriers, such as sterile isotonic saline, a phosphate buffered saline solution, water, and emulsions, such as an oil/water or water/oil emulsions.

In one embodiment of any of the methods described herein, the subject is a mammal. In different embodiments, the mammal is a mouse, a rat, a cat, a dog, a horse, a sheep, a cow, a steer, a bull, livestock, a primate, a monkey, or preferably a human.

This invention will be better understood from the Experimental Details which follow. However, one skilled in the art will readily appreciate that the specific methods and results discussed are merely illustrative of the invention as described more fully in the claims which follow thereafter.

EXPERIMENTAL DETAILS

Methods and Materials

Radioisotopes. $^{125}I$ in the form of sodium iodide was purchased from NEN, Boston, Mass. $^{188}Re$ in the form of Na perrhenate $Na^{188}ReO_4$ was eluted from a $^{188}W/^{188}Re$ generator (Oak Ridge National Laboratory (ORNL), Oak Ridge, Tenn.). $^{186}Re$ can be obtained through neutron irradiation of $^{185}Re$ in nuclear reactors, with high production levels achievable even in reactors with a moderate neuron flux.

Comparative $^{125}I$ and $^{188}Re$ uptake into the NIS-expressing cells. Both concentration dependence and kinetic experiments for $^{125}I$ and $^{188}ReO_4^-$ in hNIS-transfected (hNIS in pcDNA 3.1 plasmid) and non-transfected MDCK (Madin-Darby canine kidney) cells were performed using the methods of Weiss et al. [45] and Dai et al. [46]. To initiate $^{125}I^-$ or $^{188}ReO_4^-$ uptake, carrier-free $Na^{125}I$ or $Na^{188}ReO_4$ was mixed with unlabeled NaI or $NaReO_4$, respectively, to give a final concentration of 20 µM. The concentration of the NIS inhibitor Na perchlorate was 40 µM. $^{125}I^-/^{188}ReO_4^-$ uptake was expressed as picomoles per µg DNA; the DNA was determined for each well as in Kissane and Robbins [47]. A 4-min time point was used to estimate initial rates for kinetic experiments. Saturation kinetics were analyzed by Lineweaver-Burk plot [48].

Animal model. To investigate the binding of $^{125}I$ and $^{188}Re$ to NIS-expressing mammary tumors, a xenografted mammary adenocarcinoma model in nude mice was used. Since erbB-2 (Neu) is one of the better known human breast cancer oncogenes, a mammary tumor cell line (NAFA) induced by oncogenic Neu was used. The NAFA cell line derived from the MMTV-NeuT mouse [18] was grown in DMEM with 10% fetal bovine serum and 1% penicillin-streptomycin. Tazebay et al. previously demonstrated [31, 41] specific active iodide transport in mammary adenocarcinoma in MMTV-NeuT mice with $^{99m}TcO_4^-$ scintigraphy, confirmed by immunoblot analysis for mgNIS expression in Neu tumor. Female nude mice (Charles River Laboratories) 4-6 weeks old were injected SC with $10^6$ NAFA cells into the left groin. Ten days after injection the tumors reached 0.5-0.7 cm in diameter.

All animal experiments were performed according to the protocol approved by the Animal Institute Committee, Albert Einstein College of Medicine.

Biodistribution. Each mouse was injected IV with a mixture of 18 µCi $Na^{188}ReO_4$ and 1.7 µCi $Na^{125}I$ in 0.1 mL normal saline. In order to block mg-NIS in expressing organs and tumor, control animals were injected with the above mixture of isotopes combined with 2 mg $NaClO_4$. At 20 minutes, 2 hours and 24 hours after administering radioactivity, the animals were sacrificed, and their organs and tumors were removed, weighed and counted in a gamma counter using the energy window for $^{188}Re$ which excludes $^{125}I$ emissions. One week later, after practically all $^{188}Re$ had already decayed, the organs were counted again in the $^{125}I$ energy window. The % ID/g for each organ was determined, and RIs (% ID/g in the tumor divided by the % ID/g in normal tissue) were calculated.

Dosimetry. The self-doses to major organs and tumors from $^{131}I$ and $^{188}Re$ in humans were calculated using MIR-DOSE 3 software [29] (ORNL) applying S-values for a 70-kg reference adult. "S" is an absorbed dose per unit cumulated activity. S-values are tabulated in the Medical Internal Radiation Dose pamphlet #11 published by the Society of Nuclear Medicine. The following formula [26] was used for conversion of time-activity data in mice into time-activity data in humans:

% ID human organ=% $ID/g_{animal\ organ}$·
(body $mass_{animal}$/body $mass_{human}$)·
organ $mass_{human}$.

It should be noted that dosimetry calculations in humans were performed with the sole purpose of comparing the therapeutic efficacy and potential damage to the stomach and thyroid from $^{131}I$ and $^{188}Re$ beta-particles, thus only "self" doses were calculated. Besides, absorbed fractions for beta-particles are equal to zero in a volume larger than 1 cm$^3$ [23] and thus do not contribute significantly to the "cross-fire" effect in humans. However, in more comprehensive dosimetry calculations organ cross-irradiation from highly penetrative $^{131}I$ gamma-rays should be taken into consideration.

Statistics. Biodistribution results obtained from the same animal were compared using paired t-test; results obtained from different animals were compared using unpaired t-test. P values of <0.05 were considered statistically significant.

Results

Figure 1:
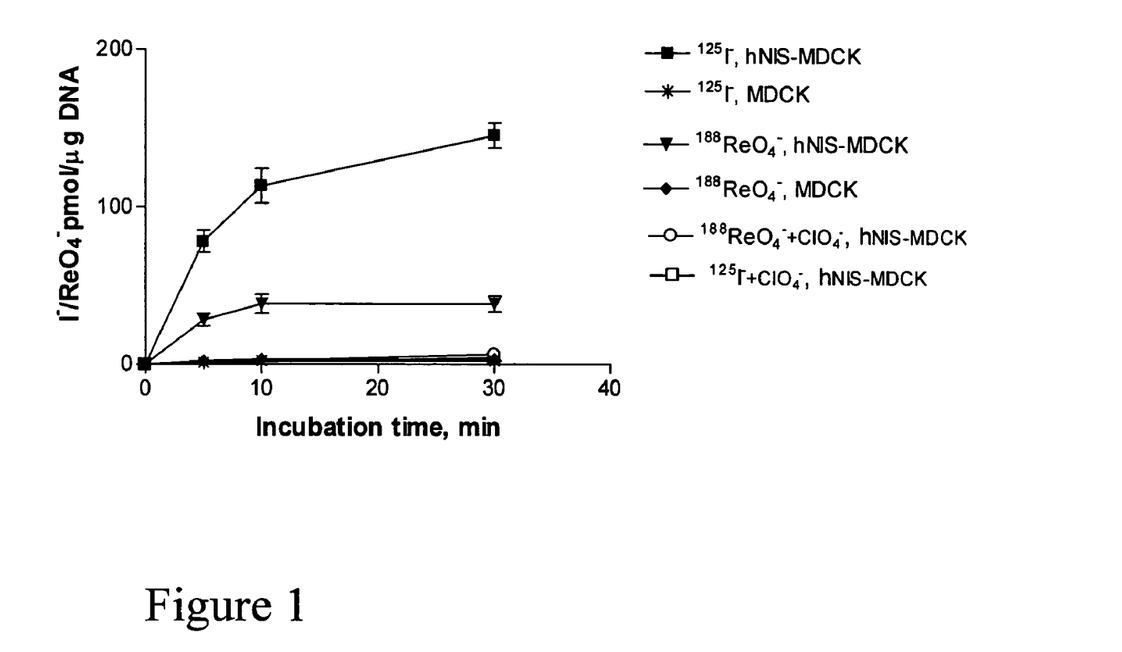
FIG. 1. Kinetic data on comparative $^{125}I^-$ and $^{188}ReO_4^-$ accumulation in hNIS-transfected and non-transfected MDCK cells.
Figure 2:
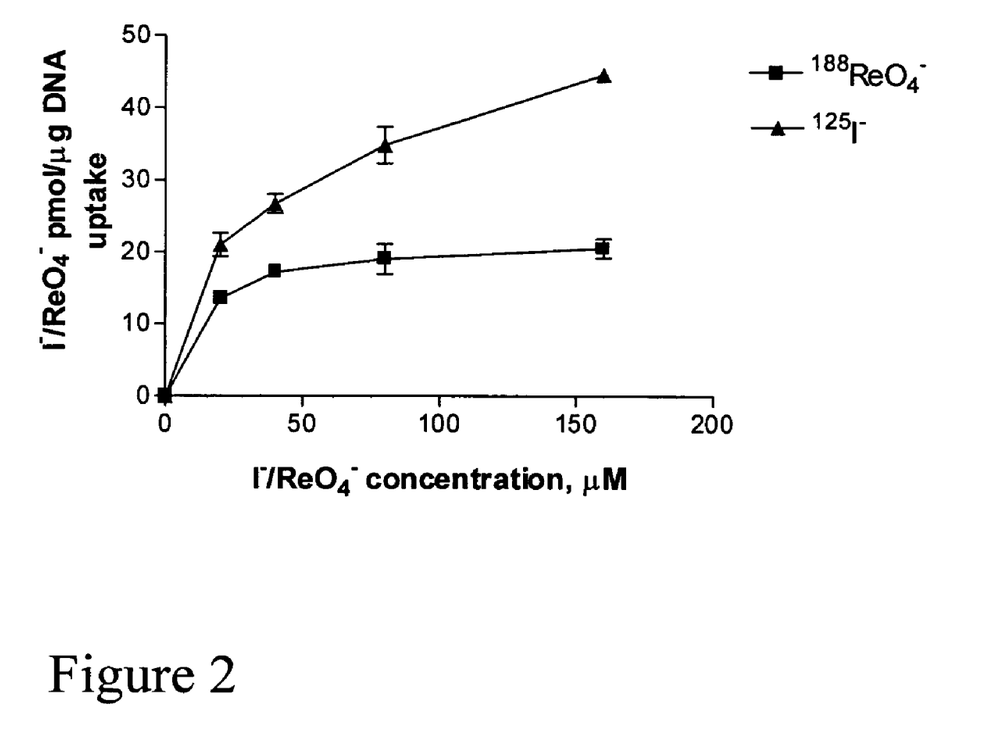
FIG. 2. Comparative $^{125}I^-$ and $^{188}ReO_4^-$ accumulation in hNIS-transfected and non-transfected MDCK cells as a function of radionuclide concentration.

In vitro studies. The comparative uptake of $^{125}I^-$ and $^{188}Re$ was determined using NIS-expressing Madin-Darby canine kidney (MDCK) cells. Kinetic data on comparative $^{125}I^-$ and $^{188}ReO_4^-$, accumulation in hNIS-transfected and non-transfected MDCK cells are presented in FIG. 1. It is obvious from these data that $^{188}ReO_4^-$ is transported by NIS with 14-fold concentration gradient in comparison to non-transfected cells. The $K_m$ (26.1 µM) determined for $^{125}I^-$ influx in MDCK cells (FIG. 2) was quite close to the $K_m$ value of 30 µM determined for $^{125}I^-$ influx in FRTL-5 cells. The $K_m$ determined for $^{188}ReO_4^-$ (12.6 µM) reveals an even higher affinity of NIS for $^{188}ReO_4^-$ than for $^{125}I^-$. The higher affinity of $^{188}ReO_4^-$ for NIS than those of such actively transported ions as $ClO_3^-$ ($K_m$=277) and $NO_3^-$ ($K_m$=739) [44] may be due to the significantly smaller ionic radii of $ClO_3^-$ and $NO_3^-$ (1.66 Å and 1.45 Å, respectively) in comparison to those of $^{188}ReO_4^-$ (1.88 Å) and $^{125}I$ (2.2 Å), which make $ClO_3^-$ and $NO_3^-$ fit too "loosely" into the binding region of the symporter.

In vivo studies. The uptake of $^{188}ReO_4^-$ compared to $^{125}I^-$ was determined in mice bearing mgNIS-expressing mammary tumors. The biodistribution results are given in Table 1. The tumors exhibited increased uptake of $^{125}I^-$ and $^{188}ReO_4^-$ in comparison with the tissues that do not express NIS (liver, muscle, spleen, kidney). The uptake in the tumors plateaued over the initial 2 hours and then decreased over a 24 hour period. There was no statistically significant difference between $^{125}I^-$ and $^{188}ReO_4^-$ % ID/g tumor at 20 minutes (P=0.05), but at later time points $^{188}ReO_4^-$ uptake was higher than that of $^{125}I^-$ (P=0.039 and 0.033 for 2 and 24 hour time points, respectively). At all 3 time points, co-administration of $ClO_4^-$, a powerful blocking agent for NIS, significantly decreased uptake of both isotopes by the stomach, salivary glands and thyroid and resulted in their rapid clearance, paralleling the blood pool. In tumors, $ClO_4^-$ co-administration caused brief but significant elevation of both isotopes uptake at 20 minutes. This can be explained by a combination of the higher concentration of $^{125}I^-$ and $^{188}ReO_4^-$ in the blood due to their decreased uptake by stomach and thyroid ("sink" effect) and, possibly, by different diffusion rates of $ClO_4^-$, $^{125}I^-$ and $^{188}ReO_4^-$ in tumor capillaries. By 2 hours, tumors were showing the same trend as other NIS-expressing tissue, i.e., decreased uptake of $^{125}I^-$ and $^{188}ReO_4^-$ in the presence of $ClO_4^-$. Without $ClO_4^-$, the thyroid continued to increase $^{125}I^-$ uptake through 24 hours, presumably due to organification, while $^{188}ReO_4^-$ was almost completely washed out of the thyroid by 24 hours.

The tumor to normal tissue ratios (RIs) shown in Table 2 exceeded unity at 20 minutes for all non-NIS expressing organs for both $^{125}I^-$ and $^{188}ReO_4^-$ and steadily increased at later time points. RIs for salivary glands were also higher than unity reflecting less NIS activity in these organs than in tumor. Lower than 1 tumor to blood ratios for 20 minutes and 2 hours may be explained by poor vascularization of the tumors which were encapsulated in fatty tissue with very few blood vessels as well as by relatively slow blood clearance of $^{125}I^-$ and $^{188}ReO_4^-$ during the first 2 hours after injection.

The results of dosimetry calculations for $^{131}I^-$ and $^{188}ReO_4^-$ administered to a reference 70-kg adult bearing a 2 g tumor are presented in Table 3. The dose delivered to the tumor by $^{188}ReO_4^-$ is 4.5 times higher than by $^{131}I^-$. The doses delivered by $^{131}I^-$ and $^{188}ReO_4^-$ to NIS-expressing tumors produce an estimated peak dose intensity of 0.1 Gy/h (10 rad/h) and are within the domain of low-dose rate radiation (LDR). In contrast, high-dose radiation (HDR), such as external-beam radiation therapy (RT), typically delivers 60 Gy/h (6000 rad/h) [20]. LDR has been shown to be effective in specific applications, such as radioimmunotherapy, through mechanisms such as cell cycle effects, induction of apoptosis, and tumor bed effects (death of adjacent, non-irradiated cells) [13].

Using S-values for the whole body from $^{131}I^-$ and $^{188}ReO_4^-$ [29], the whole body dose from $^{188}ReO_4^-$ was estimated to be ~2 times higher than from $^{131}I^-$ (0.71 rad/mCi) [23] which is generally very well tolerated. The dose to the stomach is higher for $^{188}ReO_4^-$ but is still well within the tolerance level of this organ [7]. Also, methods of decreasing $^{188}ReO_4^-$ binding to NIS in gastric mucosa, such as gastric lavage, can be employed if needed. Regarding the dose to the thyroid, it should be pointed out that while 0.93 rad/mCi from $^{188}ReO_4^-$ is the maximum dose as there is no $^{188}ReO_4^-$ present in the thyroid after 24 hours, 1.26 rad/mCi from $^{131}I^-$ within 24 hours is only a fraction of the actual dose to the thyroid, due to iodine organification, which is 1300 rad/mCi [23]. In order to protect the thyroid, exogenous thyroid hormone should be administered prior to $^{131}I$ treatment.

Figure 3A:
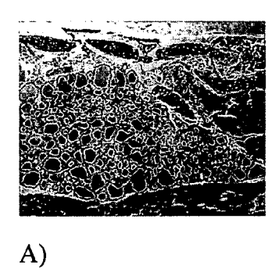
FIGS. 3A-3E. Hematoxylin and eosin stained NIS-expressing tissues from control mice and mice treated with $^{188}ReO_4^-$ or $^{131}I^-$: A) control thyroid, B) thyroid treated with 1.5 mCi $^{188}ReO_4^-$, C) thyroid treated with 50 μCi $^{131}I^-$, D) control stomach, E) stomach treated with 1.5 mCi $^{188}ReO_4^-$.
Figure 3B:
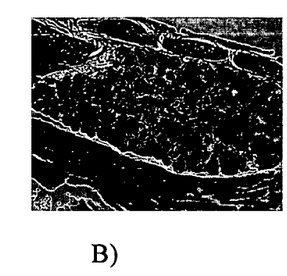
Figure 3C:
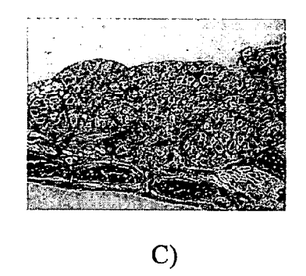
Figure 3D:
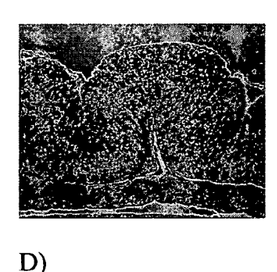
Figure 3E:
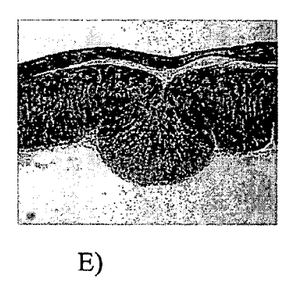

To establish the safe dose of $^{188}ReO_4^-$ to treat the NIS-expressing tumors in mice, healthy mice were treated with 1.5 mCi $^{188}ReO_4^-$ and observed for 80 days. No weight loss or other gastrointestinal toxicity was seen in treated animals. After 80 days the animals were sacrificed, their thyroids and stomachs removed and analyzed histologically. FIGS. 3A-3C present the hematoxylin and eosin stained thyroid tissue from a control mouse, a mouse treated with 1.5 mCi $^{188}ReO_4^-$, and a mouse treated with 50 µCi $^{131}I^-$. FIGS. 3D-3E show the stomachs from the control mouse and the mouse treated with 1.5 mCi $^{188}ReO_4^-$, respectively. The absence of damage by $^{188}ReO_4^-$ to normal NIS-containing structures in the mouse can be explained by the ≦1 mm thickness of these tissues in comparison with the >10 mm optimal tissue range of high-energy betas emitted by $^{188}ReO_4^-$. These results are confirmed by the well-known tolerance of gastric mucosa in patients treated with high activities of $^{131}I^-$ and indirectly by recently published therapy results in patients treated with $^{90}Y$ (which is a high energy beta-emitter like $^{188}Re$) labeled gastrin receptor ligands [40].

Figure 4:
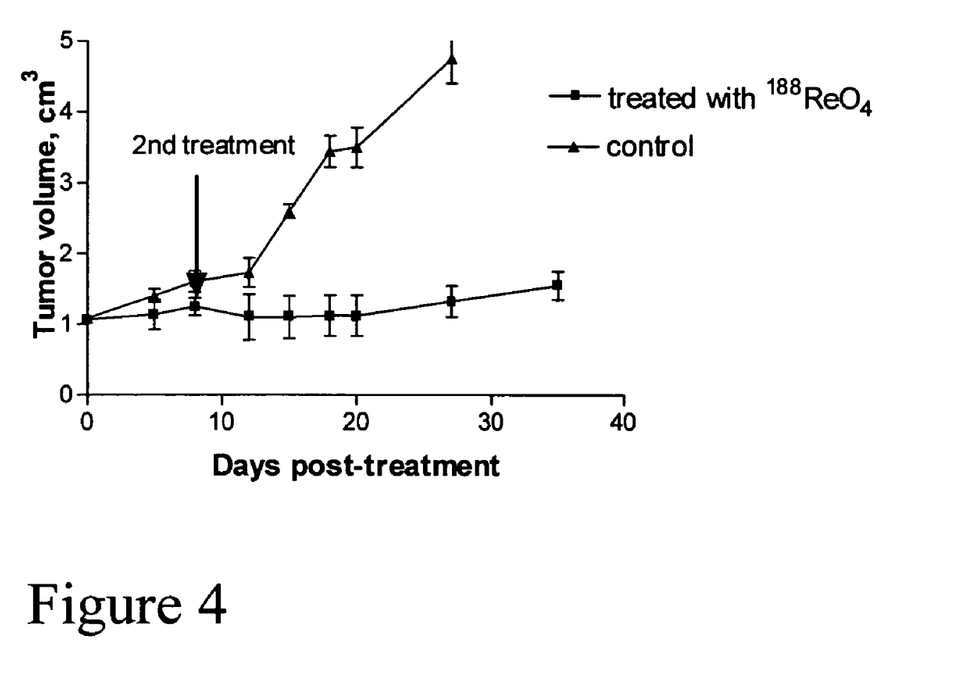
FIG. 4. Treatment of nude mice bearing NAFA cells-xenografted tumors with $^{188}ReO_4^-$.

A xenografted mammary adenocarcinoma model in nude mice was used to demonstrate the efficiency of treatment with $^{188}ReO_4^-$. When the tumors reached 0.5-0.7 cm in diameter, the animals were treated with 1.5 mCi $^{188}ReO_4^-$ followed by a $2^{nd}$ dose of 1.5 mCi $^{188}ReO_4^-$ one week later. Tumor growth stabilization was observed in treated mice in comparison with the aggressive growth of the untreated tumors (FIG. 4).

Figure 5A:
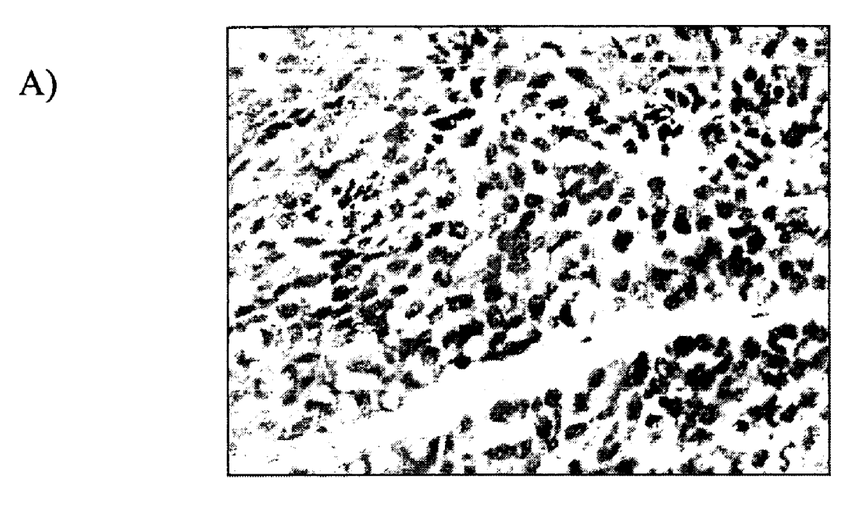
FIGS. 5A-5B. Histological analysis for apoptosis of NAFA-cells xenografts in nude mice: A) control (untreated) tumor on day 35; B) tumor from a mouse treated with 2×1.5 mCi $^{188}Re$-perrhenate, day 35 post-treatment.
Figure 5B:
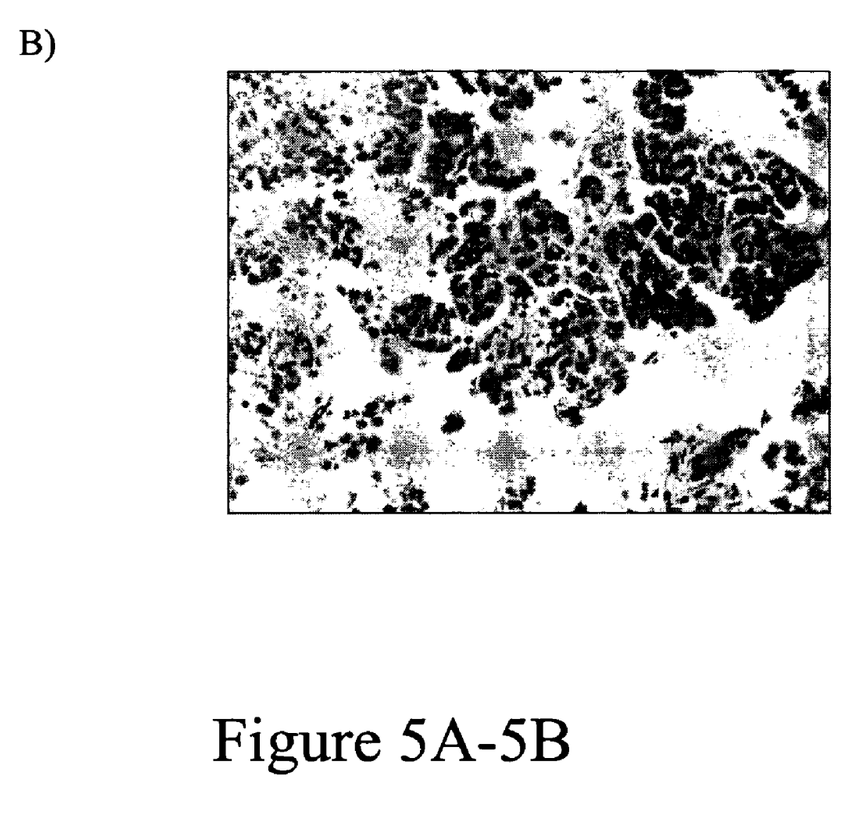

At the completion of the experimental treatment with $^{188}Re$-perrhenate, the animals were sacrificed, their tumors removed, fixed in buffered formaline, cut and analyzed for apoptosis using an Apoptag Plus® kit. Briefly, 3'-OH termini of DNA fragments, which are the hallmark of apoptosis, were labeled with digoxigenin-modified nucleotides by terminal deoxynucleotidyl transferase (TdT). This enzyme selectively detects apoptotic over necrotic cells. The labeled DNA was detected using an anti-digoxigenin antibody, and the detection was performed using a chromagen. As a result the apoptotic cells were stained brown. The results are shown in FIGS. 5A-5B, where apoptotic cells appear lightly stained in the black-and-white image. The treated tumors (FIG. 5B) showed significantly higher number of apoptotic cells in comparison with control tumors (FIG. 5A) as well as the areas of necrosis. This observation is consistent with the fact that particulate ionizing radiation is known to cause cell death through both apoptotic [13] and necrotic pathways [49, 50].

TABLE 1

Biodistribution of $^{125}I^-$ and $^{188}ReO_4^-$ in NIS-expressing xenografted mammary adenocarcinoma in nude mice.

| Time | Organ | ID/g, % (SD) | | | |
|---|---|---|---|---|---|
| | | $^{125}I^-$ | $^{125}I^- + ClO_4^-$* | $^{188}ReO_4^-$ | $^{188}ReO_4^- + ClO_4^-$ |
| 20 min | blood | 5.40 (1.68) | 10.15 (1.06) | 9.34 (3.08) | 19.79 (0.54) |
| | spleen | 1.93 (1.60) | 0.60 (0.14) | 2.77 (1.77) | 2.10 (0.94) |
| | liver | 1.83 (0.49) | 4.35 (0.64) | 3.05 (1.47) | 7.06 (1.82) |
| | kidneys | 2.38 (0.53) | 6.50 (0.28) | 3.16 (1.31) | 8.58 (2.18) |
| | muscle | 0.23 (0.06) | 0.60 (0.00) | 0.47 (0.13) | 1.02 (0.06) |
| | stomach | 29.03 (16.31) | 3.45 (0.77) | 37.03 (16.09) | 5.05 (0.84) |

TABLE 1-continued

Biodistribution of $^{125}I^-$ and $^{188}ReO_4^-$ in NIS-expressing xenografted mammary adenocarcinoma in nude mice.

| Time | Organ | ID/g, % (SD) | | | |
|---|---|---|---|---|---|
| | | $^{125}I^-$ | $^{125}I^-$ + $ClO_4^-$* | $^{188}ReO_4^-$ | $^{188}ReO_4^-$ + $ClO_4^-$ |
| | salivary glands | 1.40 (0.85) | 0.65 (0.07) | 2.64 (0.25) | 1.51 (0.03) |
| | thyroid | 5.10 (2.64) | 0.90 (0.14) | 7.47 (3.21) | 1.93 (0.10) |
| | tumor | 3.08 (0.68) | 5.85 (0.77) | 3.86 (0.97) | 9.23 (2.88) |
| 2 hr | blood | 4.10 (0.65) | 7.85 (0.91) | 6.53 (0.61) | 11.10 (1.41) |
| | spleen | 1.07 (0.99) | 2.35 (0.21) | 1.17 (0.70) | 2.09 (0.30) |
| | liver | 1.37 (0.05) | 2.25 (0.36) | 2.44 (0.28) | 4.39 (0.16) |
| | kidneys | 1.87 (0.21) | 3.75 (0.36) | 2.50 (0.29) | 4.45 (0.36) |
| | muscle | 0.43 (0.31) | 0.30 (0.00) | 0.67 (0.35) | 0.41 (0.03) |
| | stomach | 29.00 (8.13) | 3.60 (0.43) | 45.20 (10.32) | 3.47 (0.43) |
| | salivary glands | 2.30 (1.19) | 0.50 (0.14) | 6.47 (2.10) | 0.86 (0.18) |
| | thyroid | 21.10 (13.74) | 0.60 (0.14) | 13.98 (6.92) | 0.75 (0.07) |
| | tumor | 2.80 (0.91) | 1.05 (0.21) | 3.50 (0.56) | 1.35 (0.07) |
| 24 hr | blood | 0.15 (0.07) | 0.02 (0.01) | 0.28 (0.10) | 0.005 (0.001) |
| | spleen | 0.10 (0.00) | 0.010 (0.001) | 0.04 (0.01) | 0.00 (0.00) |
| | liver | 0.04 (0.01) | 0.010 (0.001) | 0.050 (0.003) | 0.003 (0.001) |
| | kidneys | 0.09 (0.01) | 0.010 (0.001) | 0.13 (0.03) | 0.001 (0.001) |
| | muscle | 0.04 (0.01) | 0.010 (0.001) | 0.032 (0.003) | 0.009 (0.001) |
| | stomach | 1.30 (0.28) | 0.020 (0.01) | 2.40 (0.28) | 0.020 (0.001) |
| | salivary glands | 0.10 (0.01) | 0.01 (0.00) | 0.14 (0.01) | 0.020 (0.001) |
| | thyroid | 42.60 (2.68) | 0.13 (0.04) | 0.20 (0.01) | 0.010 (0.001) |
| | tumor | 0.25 (0.07) | 0.060 (0.002) | 0.40 (0.05) | 0.08 (0.002) |

*2 mg $NaClO_4$ per animal was co-injected with $^{125}I^-$ and $^{188}ReO_4^-$. $ClO_4^-$ is a blocking agent for NIS.

TABLE 2

Tumor to normal organ ratio (RIs) of $^{125}I^-$ and $^{188}ReO_4^-$ in NIS-expressing xenografted mammary adenocarcinoma in nude mice.

| Time | Organ | RI | |
|---|---|---|---|
| | | $^{125}I^-$ | $^{188}ReO_4^-$ |
| 20 min | blood | 0.57 | 0.41 |
| | spleen | 1.60 | 1.39 |
| | liver | 1.68 | 1.27 |
| | kidneys | 1.29 | 1.22 |
| | muscle | 13.39 | 8.21 |
| | stomach | 0.11 | 0.10 |
| | salivary glands | 2.20 | 1.46 |
| | thyroid | 0.60 | 0.52 |
| | tumor | 1.00 | 1.00 |
| 2 hr | blood | 0.68 | 0.54 |
| | spleen | 2.62 | 2.99 |
| | liver | 2.04 | 1.43 |
| | kidneys | 1.50 | 1.40 |
| | muscle | 12.17 | 5.22 |
| | stomach | 0.11 | 0.08 |
| | salivary glands | 1.21 | 0.54 |
| | thyroid | 0.13 | 0.25 |
| | tumor | 1.00 | 1.00 |
| 24 hr | blood | 1.67 | 1.45 |
| | spleen | 2.50 | 10.00 |
| | liver | 6.25 | 8.00 |
| | kidneys | 2.77 | 3.08 |
| | muscle | 6.25 | 12.50 |
| | stomach | 0.19 | 0.17 |
| | salivary glands | 2.50 | 2.85 |
| | thyroid | 0.01 | 2.00 |
| | tumor | 1.00 | 1.00 |

TABLE 3

Doses delivered during 24 hour period by $^{131}I^-$ or $^{188}ReO_4^-$ to the selected organs and 2 g tumor in 70-kg reference adult.

| Organ | Doses, rad/mCi | |
|---|---|---|
| | $^{131}I^-$ | $^{188}ReO_4^-$ |
| spleen | 0.016 | 0.058 |
| liver | 0.028 | 0.155 |
| kidneys | 0.04 | 0.190 |
| stomach | 0.42 | 1.97 |
| thyroid* | 1.26 | 0.930 |
| tumor | 0.04 | 0.18 |

*Doses have been calculated without thyroid suppression by exogenous thyroid hormone.

TABLE 4

Comparison of the properties of $^{188}Re$, $^{186}Re$ and $^{131}I$.

| | $^{188}Re$ | $^{186}Re$ | $^{131}I$ |
|---|---|---|---|
| Energy of photons | 155 keV | 137 keV | 364 keV |
| Abundance of photons | 15% | 9% | 81% |
| Average energy of beta particles | 0.764 MeV | 0.362 MeV | 0.192 MeV |
| Half-life of radionuclides | 16.7 hours | 3.7 days | 8 days |
| Optimal tissue range of beta particles | 23-32 mm | 7-12 mm | 2.6-5 mm |

TABLE 4-continued

Comparison of the properties of $^{188}$Re, $^{186}$Re and $^{131}$I.

| | $^{188}$Re | $^{186}$Re | $^{131}$I |
|---|---|---|---|
| # atoms/g tumor for 90% cure probability at optimal range | $5.34 \times 10^{11}$ | $2.34 \times 10^{12}$ | $6.38 \times 10^{12}$ |
| Radiation dose delivered to tumor, arbitrary units | 4.5× | n.d. | 1.0× | n.d. = not determined.

Discussion

The present application demonstrates that the Na$^+$/I$^-$ symporter mediates the uptake of the powerful beta-emitting radiometal Rhenium in mammary tumors, using as an example $^{188}$Re-perrhenate. This finding is significant for the diagnosis of breast cancer and treatment of cancer. Before the present study, it was not obvious that tumors expressing a Na$^+$/I$^-$ symporter would take up ReO$_4^-$, since it had been reported that ReO$_4^-$ is a potent blocking agent for NIS in a *Xenopus* oocyte expression system [44].

The present application further demonstrates that Rhenium radioisotopes, as exemplified in the form of $^{188}$ReO$_4^-$, can effectively inhibit the in vivo growth of tumors expressing a Na$^+$/I$^-$ symporter. The application also demonstrates that in the absence of organification of the radioisotopes, Rhenium radioisotope delivers a superior radiation dose to the tumor in comparison to radioactive iodine, a finding which would not have been previously obvious. Similar to radioiodine, $^{188}$Re-perrhenate exhibited NIS-dependent uptake into the tumors, but, like $^{99m}$Tc-pertechnetate and unlike radioiodine, no long-term organification and accumulation of Rhenium occurs in the thyroid gland.

$^{188}$Re is conveniently obtained from $^{188}$W/$^{188}$Re generators [9] which are available from Oak Ridge National Laboratory (ORNL). The long half-life (69 days) of the parent $^{188}$W permits extensive distribution to nuclear medicine departments and on-site access to the radioisotope in a fashion similar to $^{99m}$Tc. The superior properties of Rhenium radioisotopes compared to those of $^{131}$I are summarized in Table 4. The emission characteristics and physical properties of $^{188}$Re, as well as those of $^{186}$Re, are superior in comparison to those of $^{131}$I. The higher energy beta particles of $^{188}$Re and $^{186}$Re ($E_{average}$=0.764 MeV for $^{188}$Re and $E_{average}$=0.362 MeV for $^{186}$Re compared to $E_{average}$=0.134 MeV for $^{131}$I) are effective over a greater range, sufficient to eradicate medium or large tumors by a "cross-fire" effect, while their lower energy and low abundance gamma photons (155 keV, 15% abundance for $^{188}$Re, and 137 keV, 9% abundance for $^{186}$Re) can be imaged yet are easier to shield than the 364 keV photons of $^{131}$I. As a consequence of their emission characteristics, the optimal tissue range is 23.0-32.0 mm for $^{188}$Re and 7.0-12.0 mm for $^{186}$Re. In contrast, the lower energy beta-particles emitted by $^{131}$I have an optimal tissue range of only 2.6-5.0 mm [22]. The number of atoms of radioisotope per gram of tumor needed to produce a cure probability of 90% at the optimal range is $6.38 \times 10^{12}$ for $^{131}$I, $2.34 \times 10^{12}$ for $^{186}$Re, and $5.34 \times 10^{11}$ for $^{188}$Re [22]. These figures clearly show that $^{188}$Re and $^{186}$Re have the potential of delivering larger doses of radiation to tumors expressing NIS than does $^{131}$I even if the uptake of $^{188}$Re-perrhenate or $^{186}$Re-perrhenate is significantly lower than that of $^{131}$I. Dosimetry calculations performed by extrapolation of biodistribution data to humans, showed that $^{188}$Re-perrhenate is able to deliver 4.5 times higher dose to the tumor than $^{131}$I. The use of Rhenium radioisotopes in especially indicated for tumors larger than 5.0 mm in diameter which cannot be covered by the emission range of $^{131}$I beta-particles.

In summary, the present study has shown that Rhenium radioisotopes, as exemplified in the form of $^{188}$ReO$_4^-$, can be used effectively to inhibit the in vivo growth of tumors expressing a Na$^+$/I$^-$ symporter and that Rhenium radioisotope delivers a superior radiation dose to the tumor in comparison to radioactive iodine. The application further discloses the use of Rhenium radioisotopes to diagnose the presence of a breast tumor that expresses a Na$^+$/I$^-$ symporter.

REFERENCES

1. A. Boland, M. Ricard, P. Opolon, J-M. Bidart, P. Yeh, S. Filetti, M. Schlumberger, and M. Perricaudet, Adenovirus-mediated transfer of the thyroid sodium/iodide symporter gene into tumors for a targeted radiotherapy, Cancer Res 60 (2000) 3484-3492.
2. N. Carrasco, Iodide transport in the thyroid gland, Biochim Biophys Acta 1154 (1993) 65-82.
3. J-Y. Cho, S. Xing, X. Liu, T. L. F. Buckwalter, L. Hwa, T. J. Sferra, I-M. Chiu, and S. M. Jhiang, Expression and activity of human Na$^+$/I$^-$ symporter in human glioma cells by adenovirus-mediated gene delivery, Gene Ther 7 (2000) 740-749.
4. E. Dadachova, J. Chapman, 188-Re(V)DMSA revisited—preparation and biodistribution of potential radiotherapeutic agent with the low kidney uptake, Nucl Med Commun 19 (1998), 173-181.
5. G. H. Daniels and D. A. Haber, Will radioiodine be useful in treatment of breast cancer? Nature Med 6 (2000) 859-860.
6. E. Deutsch, K. Libson, J. L. Vanderheyden, A. R. Ketring, H. R. Maxon, The chemistry of rhenium and technetium as related to the use of isotopes of these elements in therapeutic and diagnostic nuclear medicine, Int J Rad Appl Instrum B 13 (1986) 465-477.
7. P. J. Early, D. Bruce, M. D. Sodee, Principles and Practice of Nuclear Medicine, Mosby-Year Book, 1995.
8. M. Hoher, J. Wohrle, M. Wohlfrom, H. Hanke, R. Voisard, H. H. Osterhues, M. Kochs, S. N. Reske, V. Hombach, J. Kotzerke, Intracoronary beta-irradiation with a liquid 188-Re-filled balloon: six-month results from a clinical safety and feasibility study, Circulation 101 (2000) 2355-2360.
9. H. Kamioki, S. Mirzadeh, R. M. Lambrecht, F. F. Knapp, Jr., and K. Dadachova, 188W/188Re generator for biomedical applications, Radiochim Acta 65 (1994) 39-46.
10. M. M. Kaplan, D. A. Meier, and H. J. Dworkin, Treatment of hyperthyroidism with radioactive iodine, Endocrinol Metab Clin N Am 27 (1998) 205-223.
11. M. T. Kilbane, R. A. Ajjan, A. P. Weetman, R. Dwyer, E. W. McDermott, N. J. O'Higgins, P. P. Smyth P P, Tissue iodine content and serum-mediated 125-I uptake-blocking activity in breast cancer, J Clin Endocrinol Metab 85 (2000) 1245-1250.
12. F. F. Knapp, Jr, Rhenium-188—a generator-derived radioisotope for cancer therapy, Cancer Biother Radiopharm 13 (1998) 337-349.
13. S. J. Knox, M. L. Goris, B. W. Wessels Overview of animal studies comparing radioimmunotherapy with dose equivalent external beam radiation, Radiother Oncol 23 (1992) 111-117.
14. W. Y. Lin, J. F. Hsieh, S. C. Tsai, T. C. Yen, S. J. Wang, F. F. Knapp, Jr, A comprehensive study on the blockage of thyroid and gastric uptakes of 188Re-perrhenate in endovascular irradiation using liquid-filled balloon to prevent restenosis, Nucl Med Biol 27 (2000) 83-87.
15. R. B. Mandell, L. Z. Mandell, and C. J. Link, Jr, Radioisotope concentrator gene therapy using the sodium/iodide symporter gene, Cancer Res 59 (1999) 661-668.
16. H. R. Maxon, S. R. Thomas, V. S. Hertzberg, J. G. Kereiakes, I. W. Chen, M. I. Sperling, E. L. Saenger, Relation between effective radiation dose and outcome of radioiodine therapy for thyroid cancer, N Engl J Med 309 (1983) 937-941.
17. J. J. Min, J. K. Chung, Y. L. Lee, J. H. Shin, J. S. Yeo, J. M. Jeong, D. S. Lee, M. C. Lee, In vitro and in vivo establishment of a colon cancer cell line expressing human sodium/iodide symporter gene for radioiodine concentrator gene therapy, J Nucl Med 42 Suppl (2001) 283.
18. W. J. Muller, E. Sinn, P. K. Pattengale, R. Wallace, P. Leder, Single-step induction of mammary adenocarcinoma in transgenic mice bearing the activated c-neu oncogene, Cell 54 (1988) 105-115.
19. A. Murray, M. S. Simms, D. P. Scholfield, R. M. Vincent, G. Denton, M. C. Bishop, M. R. Price, A. C. Perkins, Production and characterization of 188-Re-c595 antibody for radioimmunotherapy of transitional cell bladder cancer, J Nucl Med 42 (2001) 726-732.
20. A. D. Murtha, Review of low-dose-rate radiobiology for clinicians, Semin Radiation Oncol 10 (2000), 133-138.
21. Y. Nakamoto, T. Saga, T. Misaki, H. Kobayashi, N. Sato, T. Ishimori, S. Kosugi, H. Sakahara, J. Konishi, Establishment and characterization of a breast cancer cell line expressing Na+/I− symporters for radioiodide concentrator gene therapy, J Nucl Med 41 (2000) 1898-1904.
22. J. A. O'Donoghue, M. Bardiès and T. E. Wheldon, Relationship between tumor size and curability for uniformly targeted therapy with beta-emitting radionuclides, J Nucl Med 36 (1995) 1902-1909.
23. G. P. Saha, Fundamentals of nuclear pharmacy, Springer, N.Y., 1997.
24. M. Schlumberger, Papillary and follicular thyroid carcinoma, N Engl J Med 338 (1998) 297-306.
25. U. Seitz, B. Neumaier, G. Glatting, J. Kotzerke, D. Bunjes, S. N. Reske, Preparation and evaluation of the rhenium-188-labelled anti-NCA antigen monoclonal antibody BW 250/183 for radioimmunotherapy of leukemia, Eur J Nucl Med 26 (1999) 1265-1273.
26. R. M. Sharkey, Personal communication.
27. H. Shimura, K. Haraguchi, A. Miyazaki, T. Endo, T. Onaya, Iodide uptake and experimental 131-I therapy in transplanted undifferentiated thyroid cancer cells expressing the Na$^+$/I$^-$-symporter gene, Endocrinology 138 (1997) 4493-4496.
28. C. Spitzweg, M. K. O'Connor, E. R. Bergert, D. J. Tindall, C. Y. Young, J. C. Morris, Treatment of prostate cancer by radioiodine therapy after tissue-specific expression of the sodium iodide symporter, Cancer Res 60 (2000) 6526-6530.
29. M. G. Stabin, MIRDOSE: Personal computer software for internal dose assessment in nuclear medicine J Nucl Med 37 (1996) 538-546.
30. A. M. Taurog in L. E. Braverman and R. D. Utiger (Eds.), The thyroid: a fundamental and clinical text, Lippincott, Williams and Wilkins, Philadelphia, 2000, pp. 61-85.
31. U. H. Tazebay, I. L. Wapnir, O. Levy, O. Dohan, L. S. Zuckier, Q. H. Zhao, H. F. Deng, P. S. Amenta, S. Fineberg, R. G. Pestell and N. Carrasco, The mammary gland iodide transporter is expressed during lactation and in breast cancer. Nature Med 6 (2000) 871-878.
32. L. S. Zuckier, E. Dadachova, Y. Li, O. Dohan and N. Carrasco, Comparative biodistribution of perrhenate, pertechnetate and iodide in NIS-expressing and non-expressing tissues of mice. J Nucl Med 42 Suppl (2001) 325.
33. Breitz H. B., Fisher D R, Weiden P L, Durham J S, Ratliff B A, Bjorn M J, Beaumier P L, Abrams P G. Dosimetry of Rhenium-186-labeled monoclonal antibodies: methods, prediction from technetium-99m labeled antibodies and results of Phase I trials. J. Nucl. Med. 34(6), 1993, p. 908-917.
34. Schoeneich, G; Palmedo, H; Dierke-Dzierzon, C; Muller, S C; Biersack, H J Rhenium-186 HEDP: palliative radionuclide therapy of painful bone metastases. Preliminary results. Scand. J. Urol. Nephrol. 31(5): 445-8, 1997.
35. Limouris-G S; Skukla-S K; Gastric uptake during Re-186 HEDP bone scintigraphy. Anticancer Res. 17(3B): 1779-81, 1997.
36. Allen S. J., Blake G. M., McKeeney D. B. et al A new radiopharmaceutical $^{186}$Re-V-DMSA for therapy of medullary carcinoma of the thyroid. Eur. J. Nucl. Med. 16: 432, 1990.
37. F. A. Mettler Jr, M. J. Guiberteau Essentials of nuclear medicine imaging. 3rd ed. New York: Grune and Stratton; 1991.
38. Bateman D N. Gastric decontamination—a view for the millennium. J Accid Emerg Med 1999; 16(2):84-6
39. Pollinger B, Duhmke E. External radiotherapy of thyroid cancer. Onkologie 2001; 24(2): 134-8.
40. Behr T M, Behe M P Cholecystokinin-B/Gastrin receptor-targeting peptides for staging and therapy of medullary thyroid cancer and Cholecystokinin-B receptor-expressing malignancies. *Semin. Nucl. Med.* 2002; 32(2): 97-109.
41. PCT International Publication No. WO 01/659988, published Sep. 13, 2001, Albert Einstein College of Medicine of Yeshiva University.
42. Cancroft E. T. et al. $^{99m}$Tc-pertechnetate scintigraphy as an aid in the diagnosis of breast masses. Radiology 106(2): 441-444, 1973.
43. Spitzweg C., Joba, W., Eisenmenger, W., Heufelder, A. E. Analysis of human sodium iodide symporter gene expression in extrathyroidal tissues and cloning of its complementary deoxyribonucleic acids from salivary gland, mammary gland, and gastric mucosa. J. Clin. Endocrinol. Metab. 83: 1746-1751, 1998.
44. Eskandari S, Loo D D, Dai G, Levy O, Wright E M, Carrasco N: Thyroid Na+/I− symporter. Mechanism, stoichiometry, and specificity. J Biol Chem. 272: 27230-27238, 1997.
45. Weiss S J, Philp N J, and Grollman E F: Iodide transport in a continuous line of cultured cells from rat thyroid. Endocrinology 114: 1090-1098, 1984.
46. Dai G, Levy O and Carrasco N: Cloning and characterization of the thyroid iodide transporter. Nature 379: 458-460, 1996.
47. Kissane J M, Robbins E: The fluorometric measurement of deoxyribonucleic acid in animal tissue with special reference to the central nervous system. J Biol Chem 233: 184-187, 1958.
48. Lineweaver H, Burk D: The determination of enzyme dissociation constants. J Am Chem. Soc. 56: 658-632, 1934.
49. Gupta V K, Park J O, Jaskowiak N T, Mauceri H J, Seetharam S, Weichselbaum R R, Posner M C. Combined gene therapy and ionizing radiation is a novel approach to treat human esophageal adenocarcinoma. *Ann Surg Oncol* 2002, 9:500-504.

50. Cornelissen M, Thierens H, De Ridder L. Interphase death in human peripheral blood lymphocytes after moderate and high doses of low and high LET radiation: an electron microscopic approach. *Anticancer Res* 2002, 22:241-245.

What is claimed is:

1. A method of treating a breast tumor that takes up $^{188}ReO_4^-$ or $^{186}ReO_4^-$ to reduce the volume of the tumor in a subject which comprises administering to the subject an amount of a Rhenium radioisotope effective to treat the tumor, wherein the amount of the Rhenium radioisotope administered to the subject is a cumulative dose between 0.5-500 mCi, wherein the Rhenium radioisotope is administered as $^{188}ReO_4^-$ or $^{186}ReO_4^-$, wherein the $^{188}ReO_4^-$ or $^{186}ReO_4^-$ is taken up by the tumor, and wherein treatment of the tumor with $^{188}ReO_4^-$ or $^{186}ReO_4^-$ reduces the volume of the tumor.

2. The method of claim 1 wherein the Rhenium radioisotope is administered in a single dose or in a fractionated manner.

3. The method of claim 1, wherein the Rhenium radioisotope is administered as $^{188}ReO_4^-$.

4. The method of claim 1, wherein the Rhenium radioisotope is administered as $^{186}ReO_4^-$.

5. A method of treating a breast tumor that takes up $^{188}ReO_4^-$ or $^{186}ReO_4^-$ to reduce the volume of the tumor in a subject which comprises administering to the subject an amount of a Rhenium radioisotope effective to treat the tumor, wherein the amount of the Rhenium radioisotope administered to the subject is a cumulative dose between 0.5-500 mCi, wherein the Rhenium radioisotope is administered as $^{188}ReO_4^-$ or $^{186}ReO_4^-$, wherein the $^{188}ReO_4^-$ or $^{186}ReO_4^-$ is taken up by the tumor, wherein a radiation dose is delivered to the tumor using the Rhenium radioisotope that is higher than the radiation dose that could be delivered to the tumor using an iodine radioisotope, where the concentration of the Rhenium radioisotope administered to the subject is the same as the concentration of the iodine radioisotope administered to the subject, and wherein treatment of the tumor with $^{188}ReO_4^-$ or $^{186}ReO_4^-$ reduces the volume of the tumor.

6. The method of claim 5, wherein the radiation dose that is delivered to the tumor using the Rhenium radioisotope is at least four-fold higher than the radiation dose that could be delivered to the tumor using the iodine radioisotope, where the concentration of the Rhenium radioisotope administered to the subject is the same as the concentration of the iodine radioisotope administered to the subject.

7. The method of claim 6, wherein the radiation dose that is delivered to the tumor using the Rhenium radioisotope is 4.5 times higher than the radiation dose that could be delivered to the tumor using the iodine radioisotope, where the concentration of the Rhenium radioisotope administered to the subject is the same as the concentration of the iodine radioisotope administered to the subject.

8. The method of claim 1, wherein gastric lavage is used to decrease the binding of the Rhenium radioisotope to a $Na^+/I^-$ symporter in the gastric mucosa.

9. The method of claim 1, wherein the subject is a mammal.

10. The method of claim 9, wherein the mammal is a human.

* * * * *